United States Patent

Acton et al.

[11] 4,301,277
[45] Nov. 17, 1981

[54] 3-DEAMINO-3-(4-MORPHOLINYL) DERIVATIVES OF DAUNORUBICIN AND DOXORUBICIN

[75] Inventors: Edward M. Acton, Menlo Park; Carol W. Mosher, Stanford, both of Calif.

[73] Assignee: SRI International, Menlo Park, Calif.

[21] Appl. No.: 199,082

[22] Filed: Oct. 20, 1980

[51] Int. Cl.³ .............................................. C07H 15/24
[52] U.S. Cl. .................................... 536/17 A; 424/180
[58] Field of Search ........................... 536/17 A, 17 R; 424/180

[56] References Cited

U.S. PATENT DOCUMENTS 4,202,967  5/1980  Tong et al. ...................... 536/17 A
4,250,303  2/1981  Wu et al. ........................ 536/17 A Primary Examiner—Blondel Hazel
Attorney, Agent, or Firm—Donovan J. De Witt

[57] ABSTRACT

Described are 3'-deamino-3'-(4-morpholinyl) derivatives of daunorubicin and doxorubicin having the formula

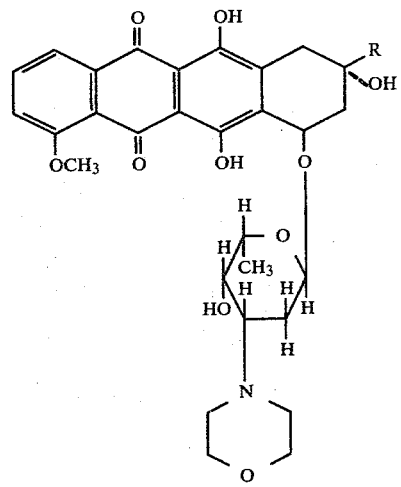

wherein R is $COCH_3$ or $-CHOHCH_3$ in the case of daunorubicin derivatives, or is $-COCH_2OH$ or $-CHOHCH_2OH$ in the case of doxorubicin derivatives together with their pharmaceutically acceptable acid addition salts. The compounds have utility as antitumor agents.

7 Claims, No Drawings

3-DEAMINO-3-(4-MORPHOLINYL) DERIVATIVES OF DAUNORUBICIN AND DOXORUBICIN

ORIGIN OF INVENTION

The invention described herein was made in the course of work under National Cancer Institute Grant No. CA25711 from the Department of Health and Human Services.

BACKGROUND OF PRIOR ART

Daunorubicin and doxorubicin derivatives wherein the amino nitrogen atom of the sugar moiety forms a part of a piperidino ring are disclosed in U.S. Pat. No. 4,202,967 issued May 13, 1980 to Tong et al and are typified by the compound N,N-pentamethylenedaunorubicin hydrochloride. This compound has a potency which is equivalent to that of daunorubicin or doxorubicin but is much lower than that of the compounds of the present invention.

SUMMARY OF INVENTION

The present invention relates to the provision of novel daunorubicin and doxorubicin derivatives having the formula

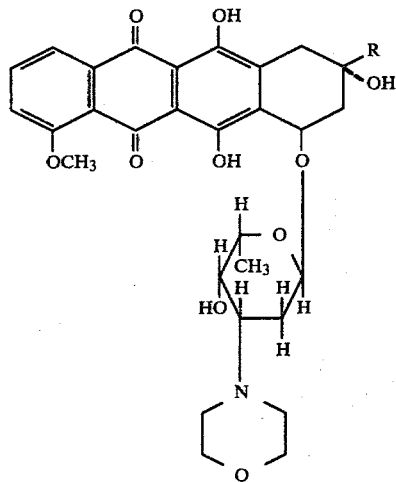

wherein R is —COCH$_3$ or —CHOHCH$_3$ in the case of daunomycin derivatives, or —COCH$_2$OH or —CHOHCH$_2$OH in the case of doxorubicin derivatives. Specifically, the invention covers the compounds 3'-deamino-3'-(4-morpholinyl) dauorubicin, 3'-deamino-3'-(4-morpholinyl)-13-dihydrodaunorubicin, 3'-deamino-3'-(4-morpholinyl) doxorubicin and 3'-deamino-3'-(4-morpholinyl)-13-dihydrodoxorubicin, together with their pharmaceutically acceptable acid addition salts. Methods for preparing these compounds, all of which are believed to have utility as antitumor agents, are set forth in the example below.

The compounds of the present invention can be prepared either in the free base or acid addition salt form. The salts are soluble in water and aqueous propylene glycol, for example, while the compounds in free base form are soluble in selected organic solvents such as chloroform, methylene chloride and ethyl acetate, for example. The salts are thus particularly well adapted for use in antitumor applications since they may be used in aqueous (including saline) solution form. These acid addition salts (prepared here as those of HCl and HBr) are preferably the pharmaceutically acceptable, non-toxic addition salts with suitable acids such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic acids, and organic sulphonic acids, for example, methanesulphonic and toluene-p-sulphonic acids.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example, a sodium barium or silver salt, of an acid in a suitable diluent, in which a resulting inorganic salt is insoluble and is thus removed from the reaction medium. An acid addition salt may also be converted into another acid addition salt by treatment with an anion exchange preparation.

The preparation of the compounds of the present invention is illustrated in the following example:

EXAMPLE

3'-Deamino-3'-(4-morpholinyl) daunorubicin hydrobromide 2

3'-Deamino-3'-(4-morpholinyl)-13-dihydrodaunorubicin hydrochloride 3

A mixture of 2,2'-oxydiacetaldehyde bis (diethyl) acetal (1) (785 mg, 3.14 mmoles) in 15 ml H$_2$O and 0.3 ml glacial acetic acid was heated under reflux for 20 minutes giving a clear solution, which was cooled. The pH was adjusted to 7, using saturated NaHCO$_3$ solution. Acetonitrile, 60 ml, and water, 20 ml, was added, followed by 1.185 g (2.1 mmoles) daunorubicin hydrochloride. The red solution was stirred for 30 minutes and then 260 mg (4.2 mmoles) NaCNBH$_3$ was added in one portion. Stirring at room temperature was continued for 2 hours when thin layer chromatography showed little or no daunorubicin. The solution was diluted with water and then extracted with chloroform. The dried extracts were concentrated, yielding 1.43 g of solid residue. This was suspended in 30 ml water and acidified to pH2 with 3 N HCl; addition of chloroform aided in dissolving the material. The chloroform layer was separated and the aqueous layer extracted with chloroform. The aqueous solution was lyophilized, leaving 725 mg of solid, largely a mixture of 2 and 3 (as hydrochlorides). This material was converted to the free bases of 2 and 3 by dissolving in 40 ml CHCl$_3$-MeOH (7:1) and shaking with saturated NaHCO$_3$ solution. The chloroform layer was washed several times with 5 ml of water, dried and concentrated to yield 675 mg solid.

Initial purification by preparative HPLC, using CH$_2$Cl$_2$-isopropanol (10:1) yielded 260 mg of still somewhat impure 2 and 355 mg of impure 3. Further purification by preparative HPLC of the 2 yielded 217 mg of 2. This was suspended in 40 ml water and dilute HBr slowly added until the pH was 4.7 and solution was complete. Lyophilization yielded the fluffy 2.HBr that was triturated with ether and collected on a filter; wt. 216 mg of 2.

The impure 3 was further purified by HPLC and then finally by reverse-phase gravity chromatography using $CH_3CN$-0.05M citrate buffer, pH4 (35:65). Homogeneous fractions were combined, made slightly alkaline by addition of $NaHCO_3$ solution, and extracted with chloroform. The chloroform solution was dried, filtered and concentrated. The residue was suspended in water, acidified to pH5 with dilute HCl; the solution was lyophilized and the hydrochloride of 3 collected by trituration with ether. Yield 100 mg.

By a practice of the methods described in the foregoing example, but with the use of doxorubicin hydrochloride rather than daunorubicin hydrochloride, there may be prepared corresponding doxorubicin derivatives such as 3'-deamino-3'-(4-morpholinyl) doxorubicin hydrobromide and 3'-deamino-3'-(4-morpholinyl)-13-dihydrodoxorubicin hydrochloride.

As indicated above, the compounds of the present invention have improved antitumor activity. This is evidenced by the data given below. In one operation, conducted in accordance with the protocol described in Cancer Chemotherapy Reports, National Cancer Institute, Vol. 3, No. 2, Part 3, September 1972, healthy mice were inoculated i.p. with Lymphocytic Leukemia P-388 ascitic fluid. The inoculated mice were then treated on days 5, 9 and 13 of the succeeding period with various amounts of chemicals 2 and 3 described in the example given above while others of the mice were similarly inoculated, for comparison purposes, with daunorubicin, doxorubicin or the N,N-pentamethylenedaunorubicin hydrochloride compound of U.S. Pat. No. 4,202,967. The average survival time of the treated mice was then determined as was that of the control mice which had been inoculated with the ascitic fluid but given no treatment with the test chemicals. Presented in the following table under the percent T/C column heading are the data so obtained. T/C values are determined by dividing the survival time of the treated mice by that of the control mice, the quotient so obtained being multiplied by 100.

Also presented in the table are the optimum dosage levels of the test chemicals (in terms of mg per kg of body weight) which produce the best antitumor response. It will be observed that the antitumor potency of the compounds of the present invention is from 20-fold to 40-fold greater than that of the danuorubicin and doxorubicin. The increase in potency as measured against that of N,N-pentamethylenedaunorubicin hydrochloride was even greater.

TABLE

| Compound | NCS Number | Optimum dose q4d 5, 9, 13 mg/kg | Survival time of treated mice/ control mice % T/C |
|---|---|---|---|
| HBr salt 2 | 327471 | 0.2 | 187 |
| 13-dihydro HCl salt 3 | 327450 | 0.4 | 153 |
| For comparison: | | | |
| N,N-Pentamethylene-adriamycin HCl salt | 271936 | 9.4 | 158 |
| Doxorubicin HCl salt | 123127 | 8 | 160 |
| Daunorubicin HCl salt | 82151 | 8 | 130 |

What is claimed is:
1. Compounds of the formula

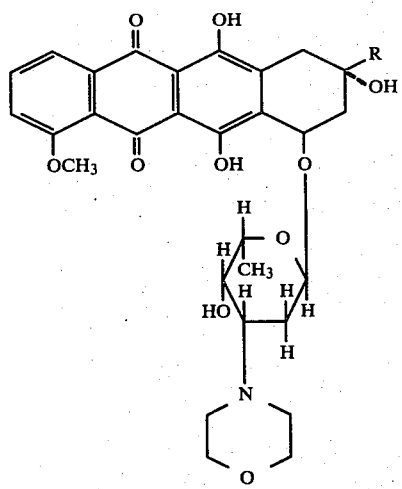

wherein R is selected from the group consisting of —$COCH_3$, —$CHOHCH_3$, —$COCH_2OH$ and —$CHOHCH_2OH$ and the pharmaceutically acceptable acid addition salts of said compounds.

2. The compound of claim 1 which is 3'-deamino-3'-(4-morpholinyl)daunorubicin and its pharmaceutically acceptable acid addition salts.

3. The compound of claim 2 which is 3'-deamino-3'-(4-morpholinyl)daunorubicin hydrobromide.

4. The compound of claim 1 which is 3'-deamino-3'-(4-morpholinyl)-13-dihydrodaunorubicin and its pharmaceutically acceptable salt.

5. The compound of claim 4 which is 3'-deamino-3'-(4-morpholinyl)-13-dihydrodoxorubicin hydrochloride.

6. The compound of claim 1 which is 3'-deamino-3'-(4-morpholinyl)doxorubicin and its pharmaceutically acceptable acid addition salts.

7. The compound of claim 1 which is 3'-deamino-3'-(4-morpholinyl)-13-dihydrodoxorubicin and its pharmaceutically acceptable acid addition salts.

* * * * *